United States Patent [19]

Tanji et al.

[11] Patent Number: 5,439,459
[45] Date of Patent: Aug. 8, 1995

[54] DISPOSABLE DIAPER HAVING SKIN-CONTACTING TOPSHEET PROVIDED WITH ELASTIC OPENING AND METHOD FOR MAKING THE ELASTIC OPENING

[75] Inventors: Hiroyuki Tanji; Ichiro Wada; Yoshio Ono; Hiroyuki Soga, all of Kawanoe, Japan

[73] Assignee: Uni-Charm Corporation, Ehime, Japan

[21] Appl. No.: 47,403

[22] Filed: Apr. 19, 1993

[30] Foreign Application Priority Data

Apr. 30, 1992 [JP] Japan ................................. 4-111859

[51] Int. Cl.⁶ ........................ A61F 13/15; B32B 31/08
[52] U.S. Cl. ...................... 604/385.2; 156/164; 156/229; 156/265
[58] Field of Search .............. 604/358, 385.1–387, 604/389–396; 156/163, 160, 164, 229, 494–496, 265

[56] References Cited

U.S. PATENT DOCUMENTS

| | | | |
|---|---|---|---|
| Re. 33,106 | 11/1989 | Beckestrom | 604/385.2 |
| 4,044,769 | 8/1977 | Papajohn | 604/385.2 |
| 4,300,967 | 11/1981 | Sigl | 156/164 |
| 4,450,026 | 5/1984 | Pieniak et al. | 156/164 |
| 4,595,441 | 6/1986 | Holvoete et al. | |
| 4,662,877 | 5/1987 | Williams | 604/385.2 |
| 4,704,115 | 11/1987 | Buell | |
| 4,704,116 | 11/1987 | Enloe | 604/385.2 |
| 4,738,677 | 4/1988 | Foreman | |
| 4,753,646 | 6/1988 | Enloe | |
| 4,846,823 | 7/1989 | Enloe | |
| 4,990,147 | 2/1991 | Freeland | 604/385.2 |
| 4,992,125 | 2/1991 | Suzuki et al. | 156/164 |
| 5,032,120 | 7/1991 | Freeland et al. | 604/385.2 |
| 5,061,261 | 10/1991 | Suzuki et al. | 604/385.2 |
| 5,110,386 | 5/1992 | Ochi et al. | 604/385.1 |
| 5,246,432 | 9/1993 | Suzuki et al. | 604/385.2 |
| 5,330,598 | 7/1994 | Erdman et al. | 604/385.2 |

FOREIGN PATENT DOCUMENTS

| | | | |
|---|---|---|---|
| 0251332 | 1/1988 | European Pat. Off. | 604/358 |
| 0403832 | 12/1990 | European Pat. Off. | |
| 0433951 | 6/1991 | European Pat. Off. | 604/385.1 |
| 2644694 | 9/1990 | France | |
| 3176053 | 7/1991 | Japan | 604/385.2 |
| 3198851 | 8/1991 | Japan | 604/385.2 |
| 2103093 | 2/1983 | United Kingdom | |
| 3280761 | 12/1991 | United Kingdom | 604/385.2 |
| 2250921 | 6/1992 | United Kingdom | 604/385.1 |
| 2255896 | 11/1992 | United Kingdom | |
| 8303051 | 9/1983 | WIPO | |
| 9108717 | 6/1991 | WIPO | |

*Primary Examiner*—Randall L. Green
*Assistant Examiner*—K. M. Reichle
*Attorney, Agent, or Firm*—Lowe, Price, LeBlanc & Becker

[57] ABSTRACT

An arrangement of a disposable diaper in which there are provided elastic members extending not only along opposite side edges of an opening formed in a skin-contacting topsheet but also further extending beyond longitudinally opposite ends of the opening substantially to longitudinally opposite ends of the skin-contacting topsheet so that the opening may sufficiently rise up together with the skin-contacting topsheet to assure reliable introduction of excretions through this opening into a pocket space defined between the skin-contacting topsheet and a separately provided topsheet underlying the skin-contacting topsheet.

4 Claims, 3 Drawing Sheets

DISPOSABLE DIAPER HAVING SKIN-CONTACTING TOPSHEET PROVIDED WITH ELASTIC OPENING AND METHOD FOR MAKING THE ELASTIC OPENING

BACKGROUND OF THE INVENTION

This invention relates to a disposable diaper having a skin-contacting topsheet provided with an elastic opening for reliable introduction of excretions and also to a method for making this elastic opening.

Japanese Utility Model Application Disclosure Gazette No. 1974-120439 discloses a diaper-cover having a topsheet formed at its central zone with an opening extending longer in the longitudinal direction than in the transverse direction of the topsheet, wherein the opening is provided along its peripheral edge with a longitudinally stretchable elastic member so as to define a closed loop-shaped elastic line. Japanese Patent Application Disclosure Gazette No. 86-41304 also discloses a disposable diaper having a topsheet formed at its central zone with an opening extending longer in the longitudinal direction than in the transverse direction of the topsheet, wherein the opening is provided along its laterally opposite side edges with elastic members, respectively.

The above-identified Japanese Utility Model Application Disclosure Gazette No. 1974-120439 and Japanese Patent Application Disclosure Gazette No. 1986-41304 disclose neither a method for forming the skin-contacting topsheet with the opening nor a method for attaching the elastic member around the opening. It is supposed that the elastic member is attached in an endless fashion along the whole periphery of the opening closely adjacent the peripheral edge and then said elastic member is covered with the peripheral edge of the opening. However, no specific method for this can be found in the specification. In view of the fact that the '439 application relates to a reusable diaper-cover, the method probably employs the cutting and sewing techniques well known in the art. According to the latter, the central portion of the sheet is cut away to form the opening and both side edges of the opening are provided with the respective elastic members bonded to the rear sides of the respective side edges with use of adhesive. Consequently, the diaper provided by the latter is not only unseemly but also is unacceptably poor in the desired strength along the peripheral edge of the opening because the elastic members are not covered at all though they are provided on the rear side of the sheet. Moreover, such an arrangement will not result in the formation of neatly uniform gathers along the whole peripheral edge of the opening and therefore it can not be expected that the whole peripheral edge of the opening tightly bears against the wearer's skin.

With both the diaper-cover and the diaper disclosed in the above identified Japanese Utility Model Application Disclosure Gazette No. 1974-120439 and Japanese Patent Application Disclosure Gazette No. 1986-41304, the opening is elasticized by the elastic member attached thereto so that the periphery thereof tends to rise up from a separately provided topsheet underlying the skin-contacting topsheet. However, the skin-contacting topsheet is provided only around the periphery of the opening with the elastic member and, consequently, the desired degree of such rising effect can not be expected from this well known arrangement. In other words, no adequate space can be obtained between the skin-contacting topsheet centrally formed with the opening and the separately provided topsheet underlying said skin-contacting topsheet. Accordingly, this space often can not serve as a pocket into which excretions should be reliably introduced and the wearer's skin may be undesirably smeared with excretions. Such inconvenience will occur particularly when the diaper is tightly worn on the wearer's body with the skin-contacting topsheet being pressed against the crotch zone of the wearer.

In view of such a problem, it is a principal object of the invention to provide a novel arrangement of a disposable diaper in which there are provided elastic members extending not only along opposite side edges of the opening but also further beyond longitudinally opposite ends of the opening substantially to the longitudinally opposite ends of the skin-contacting topsheet so that the skin-contacting topsheet centrally formed with the opening may rise up from the separately provided topsheet underlying the skin-contacting topsheet by an extent sufficient to form a desired pocket space.

SUMMARY OF THE INVENTION

In view of the object set forth above, the invention resides first in a disposable diaper having a skin-contacting topsheet formed with an elastic opening, said diaper comprising a liquid-impermeable first topsheet, a liquid-impermeable backsheet, a liquid-absorbent core sandwiched between said first topsheet and said backsheet, and a liquid-resistant second topsheet overlying said first topsheet to define said skin-contacting topsheet, said second topsheet being formed substantially at its central zone with said opening extending longer in the longitudinal direction than in the transverse direction of the second topsheet, said second topsheet being bonded along its outer periphery to said first topsheet and longitudinally stretchable elastic members being attached onto said second topsheet along opposite side edges of said opening, characterized by that said elastic members comprise first and second elastic members provided independently of each other so as to extend along opposite side edges of said opening, and to terminate substantially in longitudinally opposite ends of said second topsheet.

Preferably, said second topsheet comprises first and second sheet members.

Preferably, said first and second sheet members are bonded to each other along mutually opposed inner edges in the proximities of longitudinally opposite ends of these first and second sheet members.

Preferably, said first and second elastic members intersect or contact each other at longitudinally opposite ends of said opening.

The invention resides also in a method to form the skin-contacting topsheet of such novel diaper with the elastic opening, comprising steps of:

A. feeding continuous first and second elastic members both maintained under elongation onto a first continuous web longitudinally thereof so that said first and second continuous elastic members extend on the central zone of said first continuous web transversely spaced from the first and second side edges opposed to each other, said first and second continuous elastic members are spaced from each other transversely of said first continuous web as alternating describing crests and relatively wide troughs, with the respective crests described by said first continuous elastic member being opposed to middle portions of the respective troughs described by said second continuous elastic member and the respective crests described by said second continuous elastic member being opposed to middle portions of the respective troughs described by said first continuous elastic member, and simultaneously bonding said first and second elastic members together utilizing an adhesive to form a first continuous composite web;

B. bonding a second continuous web to the first continuous composite web over the area thereof within which the first and second continuous elastic members are fixed to the first continuous composite web to form a second continuous composite web;

C. cutting away the part of the second continuous composite web defined between the first and second continuous elastic members extending in parallel to and spaced from each other transversely of the second continuous composite web along the respective crests and troughs so as to form cutouts destined to define said openings and thereby to form third (A) and (B) continuous composite web members;

D. longitudinally shifting said third (A) and (B) continuous composite web members relative to each other so that the respective crests of the third (A) and (B) continuous composite web members are symmetrically opposed to each other in an overlapping relationship transversely of these third (A) and (B) continuous composite web members and the respective troughs thereof are also symmetrically opposed to each other but define therebetween the respective openings; and E. cutting said third (A) and (B) continuous composite web members transversely thereof along imaginary lines vertically dividing the respective pairs of mutually opposed crests in halves.

Preferably, said step D includes a step of bonding said third (A) and (B) continuous composite web members in an overlapping relationship to each other along inner side edges of the respective pairs of mutually opposed crests.

Under contractile force of the elastic members extending along the opposite side edges of the opening and further extending beyond the longitudinally opposite ends of the opening substantially to the longitudinally opposite ends of the second topsheet (i.e., the skin-contacting topsheet), said second topsheet rises up from the first topsheet underlying this most significantly around the opening and the portions of said elastic members extending between the longitudinally opposite ends of the opening and the longitudinally opposite ends of the second topsheet, thus preventing the opening from laterally shifting because these portions of the elastic members should be necessarily positioned along the center line of the crotch zone when the diaper is properly worn on the wearer's body.

BRIEF DESCRIPTION OF THE DRAWINGS

The invention will be described by way of example in reference with the accompanying drawings, in which.

PREFERRED EMBODIMENT OF THE INVENTION

First, the diaper constructed according to the invention will be described by way of example in reference with the drawings.

Figure 1:
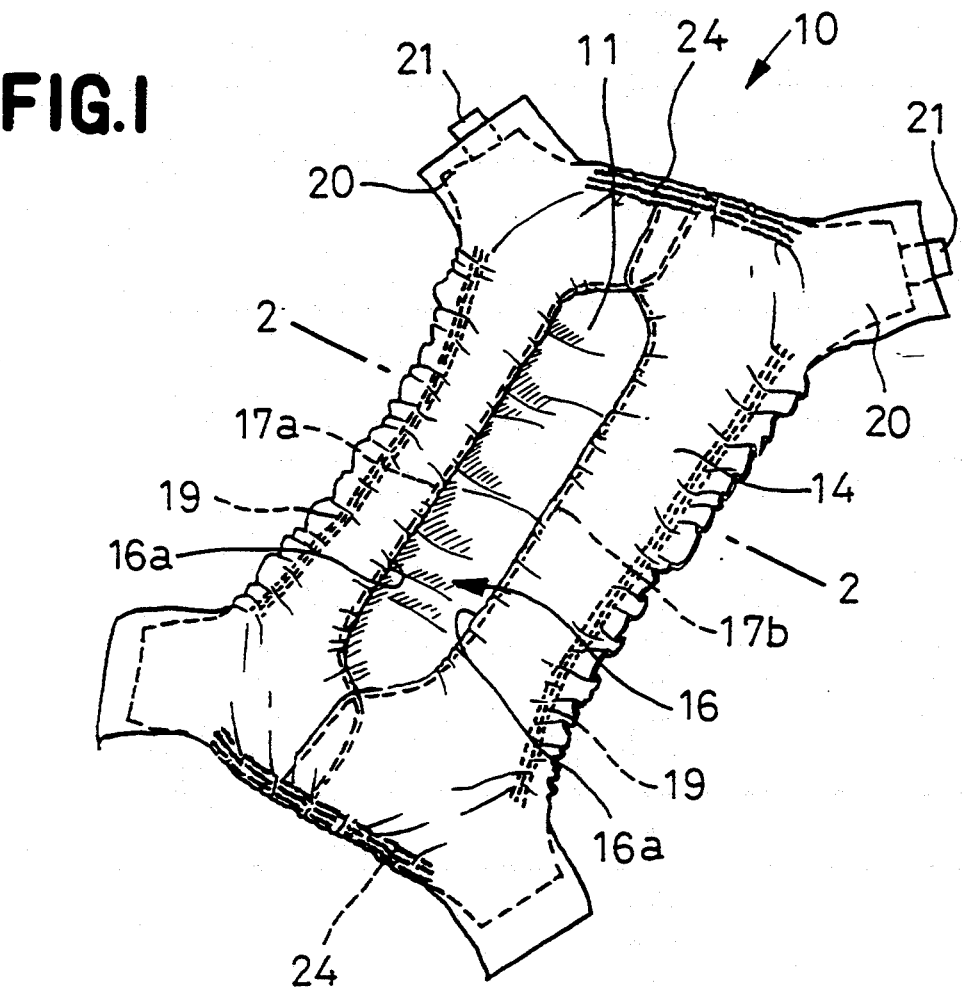
FIG. 1 is a perspective view showing an inner side of a disposable diaper having a skin-contacting topsheet constructed according to the invention.
Figure 2:
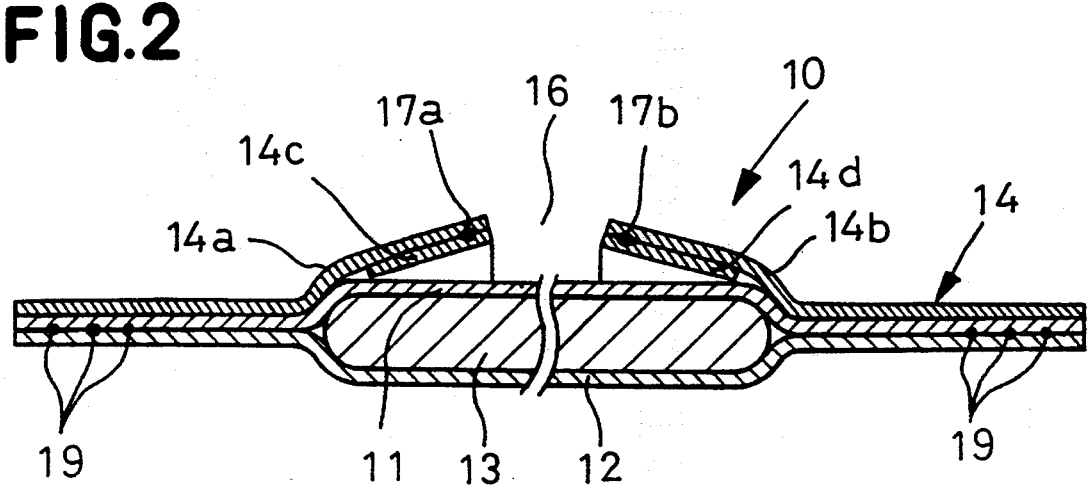
FIG. 2 is a sectional view taken along a line 2—2 in FIG. 1.

Referring to FIGS. 1 and 2, a diaper 10 comprises a liquid-permeable first topsheet 11, a liquid-impermeable backsheet 12, a liquid-absorbent core 13 sandwiched therebetween, and a liquid-resistant second topsheet 14 overlying the first topsheet 11. The second topsheet 14 is centrally formed with an opening 16 which is longer in the longitudinal direction than in the transverse direction of this sheet 14 and has longitudinally opposite ends describing circular arcs, respectively. The opening 16 may be formed at least within the crotch zone.

The second topsheet 14 actually comprises a pair of sheet members 14a, 14b overlapping side by side and having mutually opposed inner side edges, respectively, which are formed with cutouts 16a so that each pair of mutually opposed cutouts will form the opening 16. Reinforcing sheet members 14c, 14d made of the same material used as that for the sheet members 14a, 14b are bonded to rear sides of the respective cutouts 16a along edges thereof and there are provided longitudinally stretchable first and second elastic members 17a, 17b, each comprising a plurality of elastic threads, attached under elongation between the sheet members 14a, 14b and the reinforcing sheet members 14c, 14d along those edges of the respective cutouts 16a with use of hot melt type adhesive (not shown). These first and second elastic members 17a, 17b extend further beyond the longitudinally opposite ends of the opening 16 substantially to the longitudinally opposite ends of the sheet members 14a, 14b. The mutually opposed inner edges of the respective sheet members 14a, 14b are overlapped and bonded together in the proximities of the respective sheet members' longitudinally opposite ends with use of hot melt type adhesive (not shown).

The first and second elastic members 17a, 17b are provided independently of each other in contrast with a single continuous elastic member forming an endless loop as conventionally employed by the aforesaid known diaper-cover and, in addition, the mutually opposed inner side edges of the respective sheet members 14a, 14b overlapping in the proximities of the longitudinally opposite ends thereof are bonded together utilizing hot melt type adhesive. Such unique arrangement allows the second topsheet 14 to be easily torn off along said overlapping inner side edges when it is desired to expose almost the whole surface of the first topsheet 11 underlying the second topsheet 14 and thereby to scrape off solid excretion held between the first topsheet 11 and the second topsheet 14. Although said overlapping inner side edges are bonded together utilizing said adhesive, the hot melt type adhesive usually used for assembling of such diaper generally has not sufficient bonding force, even after cured, to make the operation of said tearing off difficult.

Liquid excretion is introduced through the opening 16 onto the first topsheet 11 and absorbed by the core 13 while solid excretion is introduced into a pocket space defined between the first topsheet 11 and the second topsheet 14. Such solid excretion can be scraped off from the first topsheet 11 exposed over a desired extent with the second topsheet 14 that has been torn off from the longitudinally opposite ends of the opening 16.

Between laterally opposite edges of the topsheet 11 and laterally opposite edges of the backsheet 12 both extending outward from both sides of the liquid-absorbent core 13, a plurality of elastic members 19 each comprising, in turn, a plurality of elastic threads, are attached under their stretched states with use of hot melt type adhesive (not shown), respectively, so as to be stretchable longitudinally of the sheets and fit tightly around the wearer's legs. Similarly, between longitudinally opposite ends of the topsheet 11 and the associated ends of the backsheet 12, there are provided a plurality of elastic members 24 each comprising, in turn, a plurality of elastic threads, respectively, so as to be stretchable transversely of the sheets and to fit tightly around the wearer's waist.

The topsheet 11 may be made of nonwoven fabric, porous plastic film or the like, the backsheet 12 may be made of plastic film, laminated sheet of this plastic film and nonwoven fabric or the like, the liquid-absorbent core 13 may be made of a mixture of fluff pulp and high absorption polymer powder or the like. The skin-contacting topsheet 14 and the reinforcing sheet members 14c, 14d are preferably made of water-repellent and highly air-permeable nonwoven fabric. It should be understood that, in this description of the invention, the "liquid-resistant" material refers to the material having a sufficient degree of water-repellence to prevent liquid excretion from easily penetrating therethrough with the diaper being worn on the wearer's body.

Referring to FIG. 1, the diaper 10 has two pairs of wing-like flaps 20 extending outward from laterally opposite sides of the waist line, respectively, and free ends of tape fasteners 21 attached to respective rear side wing-like flaps 20 may be adhesively secured to the backsheet 12 on the front side to erect the diaper 10 around the wearer's body.

Now the method of the invention will be described by way of example in reference with FIGS. 3 through 6.

Figure 3:
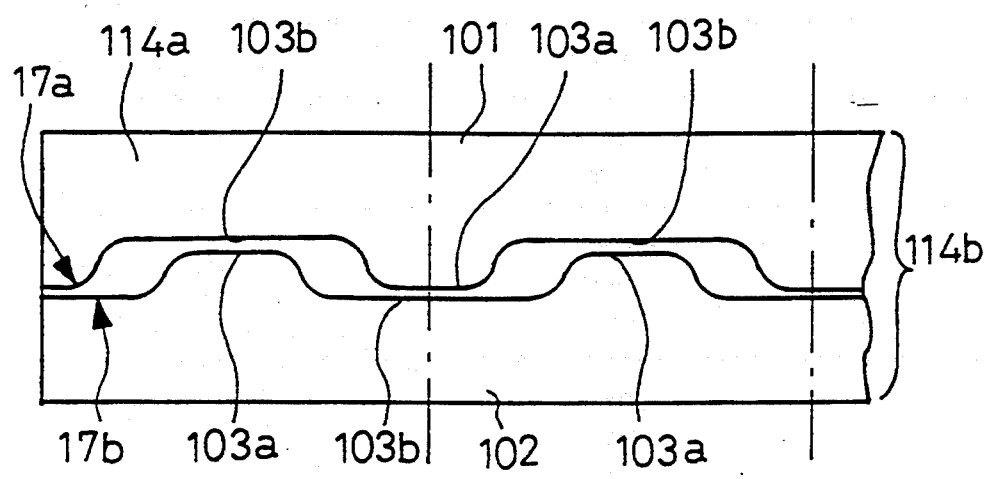
FIG. 3 is a schematic plan view illustrating a manner in which first and second elastic members are attached to a first continuous web used as the starting material for a second topsheet (i.e., the skin-contacting topsheet) to form the first continuous composite web.

Referring to FIG. 3, first and second continuous elastic members 17a, 17b both maintained under elongation are fed by traverse means (not shown) onto a first continuous web 114a longitudinally thereof so that said first and second continuous elastic members 17a, 17b extend along a central portion of said first continuous web 114a which is spaced from transversely opposite first and second side edges 101, 102 of said first continuous web 114a, said first and second continuous elastic members 17a, 17b are spaced from each other transversely of said first continuous web 114a and alternately describe crests 103a and relatively wide troughs 103b, respectively, with the respective crests 103a described by said first continuous elastic member 17a being opposed to middle portions of the respective troughs 103b described by said second continuous elastic member 17b while the respective crests 103a described by second continuous elastic member 17b are opposed to middle portions of the respective troughs 103b described by said first continuous elastic member 17a, and said first and second elastic members 17a, 17b are bonded to said first continuous web 114a utilizing hot melt type adhesive (not shown) in order to form a first continuous composite web 114b.

Figure 4:
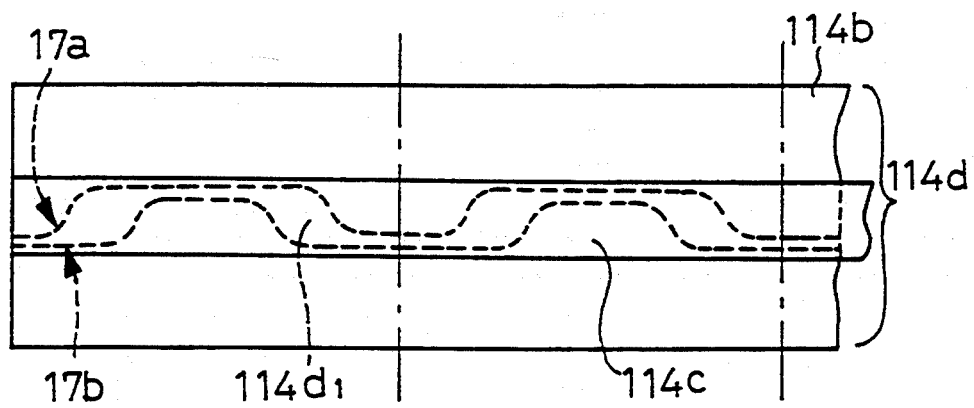
FIG. 4 is a schematic plan view illustrating a manner in which a second continuous web is bonded to said first continuous composite web over the area within which the first and second elastic members are attached so as to form a second continuous composite web.

Referring to FIG. 4, a second continuous web 114c which is narrower than the first continuous composite web 114b is bonded to the first continuous composite web 114b utilizing hot melt type adhesive (not shown) along the area thereof within which the first and second continuous elastic members 17a, 17b are fixed to the first continuous composite web 114b in order to form a second continuous composite web 114d.

Figure 5:
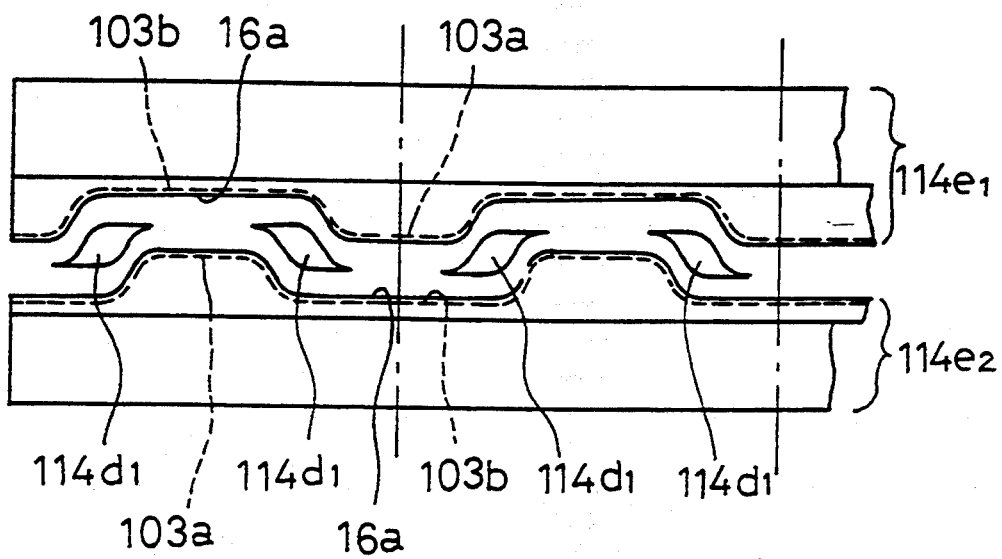
FIG. 5 is a schematic plan view illustrating a manner in which the portion of said second continuous composite web defined between the first and second elastic members is cut away to form third (A) and (B) continuous composite web members.

Referring to FIGS. 4 and 5, the part $114d_1$ of the second continuous composite web 114d defined between the first continuous elastic member 17a and the second continuous elastic member 17b extending in parallel to and spaced from each other transversely of the second continuous composite web 114d is cut away between the crests 103a and troughs 103b so as to form cutout lines 16a destined to define said openings 16 and thereby to form cutout third and fourth continuous composite web members $114e_1$, $114e_2$.

Figure 6:
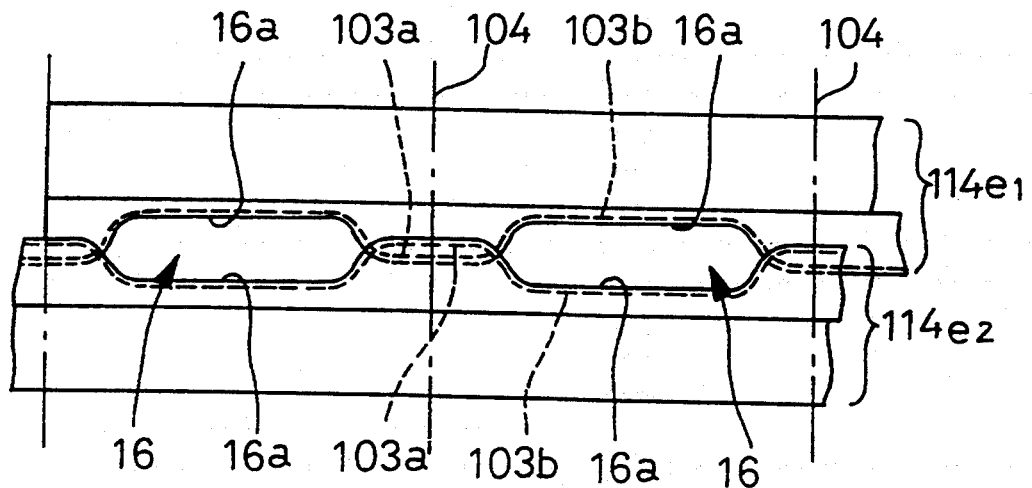
FIG. 6 is a schematic plan view illustrating a manner in which the third (A) and (B) continuous composite web members are longitudinally shifted relative to each other so that openings are defined therebetween.

Referring to FIG. 6, the third and fourth continuous composite web members $114e_1$, $114e_2$ are longitudinally shifted relative to each other so that the respective crests 103a of the third and fourth continuous composite web members $114e_1$, $114e_2$ are symmetrically opposed to each other in an overlapping relationship transversely of these third and fourth continuous composite web members $114e_1$, $114e_2$ and the respective troughs 103b (or the lines 16a) thereof are also symmetrically opposed to each other but spaced apart to define openings 16. Then, the third and fourth continuous composite web members $114e_1$, $114e_2$ are bonded together in an overlapping relationship utilizing hot melt type adhesive (not shown) along the inner side edges of the respective pairs of overlapping crests 103a. It should be understood that these inner side edges may be left not bonded, if desired.

The third and fourth continuous composite web members $114e_1$, $114e_2$ are cut transversely thereof along imaginary lines 104 vertically dividing the respective pairs of overlapping crests 103a in halves. This step of cutting may be performed with the third and fourth continuous composite web members $114e_1$, $114e_2$ being placed on the uppermost layer of the continuous diaper web which comprises a plurality of individual diapers as illustrated by FIGS. 1 and 2 (except for absence of the second topsheet 14) to obtain the individual diaper 10 of FIGS. 1 and 2.

The method for making such continuous diaper web comprising a plurality of individual diapers 10 as illustrated by FIG. 1 (except for absence of the second topsheet 14) which are successively continuous with one another longitudinally thereof is well known to those skilled in the art from various patent specifications and therefore details of such method will not be described here.

While the embodiment has been illustrated and described with respect to so-called open type diapers utilizing the tape fasteners to close the waist line around the wearer's waist, the invention will be applicable also to so-called pant-type diapers (inclusive of training pants) having a continuous waist line.

With the diaper of the invention, as will be readily understood from the foregoing description, the contractile force of the elastic members extending along the opposite side edges of the opening and extending further beyond the longitudinally opposite ends of the opening substantially to the longitudinally opposed ends of the second topsheet (i.e., the skin-contacting topsheet) allows the second topsheet to rise up from the first topsheet underlying the second topsheet most significantly around the opening and thereby allows the first and second topsheet to form therebetween a pocket space sufficient to assure reliable introduction of excretions. In addition, the portions of the elastic members extending between the respective longitudinally opposed ends and the respective longitudinally opposite ends serve to prevent the opening from laterally shifting because said portions of the elastic members should be necessarily positioned along the center line of the crotch zone when the diaper is properly worn on the wearer's body, and thus excretions reliably flows through the opening into the pocket space.

A pair of the sheet members having the respective inner edges of the opening along which the first and second elastic members are independently extend and are fixed are placed side by side in a symmetric relationship to form the second topsheet so that the mutually opposed inner side edges of the respective sheet members extending from the respective longitudinally opposite ends of the opening to the respective longitudinally opposite ends of the second topsheet can be easily separated from each other. Namely, the second topsheet can be easily torn off so as to expose the first topsheet underlying the second topsheet over a desired extent and thereby solid excretion held on the first topsheet can be effectively scraped off.

The method to form the elastic opening according to the invention allows the first and second elastic members attached to the peripheral edge of the opening to be covered with the same material used as that for said second topsheet and thereby allows formation of the seemly elastic opening to be facilitated.

What is claimed is:

1. A method of forming a disposable diaper with an elastic opening which comprises the steps of
   (A) feeding first and second continuous elastic members ($17a$, $17b$) both maintained under elongation onto a first continuous web ($114a$) longitudinally thereof so that said first and second continuous elastic members ($17a$, $17b$) extend along a central portion of said first continuous web ($114a$) and are spaced from transversely opposite first and second side edges ($101$, $102$) of said first continuous web, said first and second continuous elastic members ($17a$, $17b$) are spaced from each other transversely of said first continuous web ($114a$) and alternately describe crests ($103a$) and relatively wide troughs ($103b$) with the respective crests ($103a$) described by said first continuous elastic member ($17a$) being opposed to middle portions of the respective troughs ($103b$) described by said second continuous elastic member ($17b$) while the respective crests ($103a$) described by said second continuous elastic member ($17b$) are opposed to middle portions of the respective troughs ($103b$) described by said first continuous elastic member ($17a$) and simultaneously bonding said first and second elastic members to said first continuous web ($114a$) with use of adhesive in order to form a first continuous composite web ($114b$);
   (B) bonding a second continuous web ($114c$) to the first continuous composite web ($114b$) over an area thereof within which the first and second continuous elastic members ($17a$, $17b$) are fixed to the first continuous composite web ($114b$) in order to form a second continuous composite web ($114d$);
   (C) cutting away portions ($114d_1$) of the second continuous composite web in the space defined between the first continuous elastic member ($17a$) and the second continuous elastic member ($17b$) so as to form cutout lines ($16a$) destined to define openings ($16$) and to also thereby form third and fourth continuous composite web members ($114e_1$ and $114e_2$);
   (D) longitudinally shifting said third and fourth continuous composite web members ($114e_1$ and $114e_2$) relative to each other so that respective crests ($103a$) of said third and fourth continuous composite web members ($114e_1$ and $114e_2$) are symmetrically opposed to each other in an overlapping relationship transversely of these third and fourth continuous composite web members and respective troughs ($103b$) thereof are also symmetrically opposed to each other but spaced apart to define openings ($16$); and
   (E) cutting said third and fourth continuous composite web members ($114e_1$ and $114e_2$) transversely thereof along imaginary lines vertically dividing the respective pairs of overlapping crests ($103a$) in halves.

2. The method as cited in claim 1 wherein said step D includes the step of bonding said third and fourth continuous composite web members ($114e_1$ and $114e_2$) together in said overlapping relationship to each other along inner side edges of said overlapping crests ($103a$).

3. A method of forming a disposable diaper with an elastic opening which comprises the steps of
   (A) feeding first and second continuous elastic members ($17a$, $17b$) that are both maintained under elongation onto a first continuous web ($114a$) having transversely opposite first and second side edges ($101$, $102$), longitudinally thereof so that said first and second continuous elastic members ($17a$, $17b$) extend along a central portion of said first continuous web ($114a$) which is spaced from said transversely opposite first and second side edges ($101$, $102$), said first and second continuous elastic members ($17a$, $17b$) being spaced from each other transversely of said first continuous web ($114a$) and alternately describing crests ($103a$) and wide troughs ($103b$) having middle portions, the respective crests ($103a$) described by said first continuous elastic member ($17a$) being opposed to said middle portions of the respective troughs ($103b$) described by said second continuous elastic member ($17b$) while the respective crests ($103a$) described by said second continuous elastic member ($17b$) are opposed to middle portions of the respective troughs ($103b$) described by said first continuous elastic member ($17a$) and simultaneously bonding said first and second elastic members to said first continuous web ($114a$) with the use of adhesive in order to form a first continuous composite web ($114b$);
   (B) bonding a second continuous web ($114c$) to the first continuous composite web ($114b$) over the area thereof within which the first and second continuous elastic members ($17a$, $17b$) are fixed to the first continuous composite web (114b) in order to form a second continuous composite web (114d);

(C) cutting away portions (114d₁) of the second continuous composite web in the space defined between the first continuous elastic member (17a) and the second continuous elastic member (17b) so as to form cutout lines (16a) destined to define openings (16) and to also thereby form third and fourth continuous composite web members (114e₁ and 114e₂);

(D) longitudinally shifting said third and fourth continuous composite web members (114e₁ and 114e₂) relative to each other so that respective crests (103a) of said third and fourth continuous composite web members (114e₁ and 114e₂) are symmetrically opposed to each other in an overlapping relationship transversely of these third and fourth continuous composite web members and respective troughs (103b) thereof are also symmetrically opposed to each other but spaced apart to define openings (16); bonding said third and fourth continuous composite web members (114e₁ and 114e₂) together in an overlapping relationship to each other along inner side edges of said overlapping crests (103a); and (E) cutting said third and fourth continuous composite web members (114e₁ and 114e₂) transversely thereof along imaginary lines vertically dividing the respective pairs of overlapping crests (103a) in halves.

4. The method of claim 3, wherein in step (D) said first and second elastic members (17a, 17b) intersect each other at longitudinally opposite ends of each said opening (16).

* * * * *